United States Patent [19]
Kopelman et al.

[11] Patent Number: 6,143,558
[45] Date of Patent: *Nov. 7, 2000

[54] OPTICAL FIBERLESS SENSORS FOR ANALYZING CELLULAR ANALYTES

[75] Inventors: Raoul Kopelman, Ann Arbor; Heather Clark, Ypsilanti; Eric Monson, Ann Arbor; Stephen Parus, Ann Arbor; Martin Philbert, Ann Arbor, all of Mich.; Bjorn Thorsrud, Lima, Ohio

[73] Assignee: The Regents of the University of Michigan, Ann Arbor, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/889,538

[22] Filed: Jul. 8, 1997

[51] Int. Cl.$^7$ ..................................................... C12N 5/00
[52] U.S. Cl. ................................. 435/325; 435/4; 435/29; 422/82.05; 422/82.06; 436/164; 436/172
[58] Field of Search .................................. 435/29, 325, 4; 422/82.06, 82.05; 436/164, 172

[56] References Cited

U.S. PATENT DOCUMENTS

| | | | |
|---|---|---|---|
| 4,945,171 | 7/1990 | Haughland et al. | 549/224 |
| 5,361,314 | 11/1994 | Kopelman et al. | . |
| 5,627,922 | 5/1997 | Kopelman et al. | . |
| 5,691,205 | 11/1997 | Kawabata et al. | 436/125 |

OTHER PUBLICATIONS

Tan et al. Science, 258:778, 1992.
Grabar et al., "Preparation and Characterization of Au Colloid Monolayers," *Analytical Chemistry* 67(4):735–743 (1995).
Freeman et al., "Self–Assembled Metal Colloid Monolayers: An Approach to SERS Substrates," *Science* 267:1629–1632 (1995).
Grabar et al., "Kinetic Control of Interparticle Spacing in Au Colloid–Based Surfaces: Rational Nanometer–Scale Architecture," *J. Am. Chem. Soc.* 118:1148–1153 (1996).
Geoghegan et al., "Adsorption of Horseradish Peroxidase, Ovomucoid and Anti–immunoglobulin to Colloidal Gold for the Indirect Detection of Concanavalin A, Wheat Germ Agglutinin and Goat Anti–Human Immunglobulin G on Cell Surfaces at the Electron Microscopic Level: A New Method, Theory and Application," *J. of Histochemistry and Cytochemistry* 25(11):1187–1200 (1977).
Handley et al., "Colloidal gold–low density lipoprotein conjugates as membrane receptor probes," *Proc. Natl. Acad. Sci. USA* 78(1):368–371 (1981).
Roe et al., "A Model of Protein–Colloidal Gold Interactions," *J. of Histochemistry and Cytochemistry* 35(11):1191–1198 (1987).
Handley et al., "Hepatic Binding and Internalization of Low Density Lipoprotein–Gold Conjugates in Rats with 17α–Ethinylestradiol," *J. of Cell Biology* 90:778–787 (1981).
Godwin et al., "A Flourescent Zinc Probe Based on Metal–Induced Peptide Folding," *J. Am. Chem. Soc.* 118:6514–6515 (1996).
Blyth et al., "Sol–Gel Encapsulation of Metalloproteins for the Development of Optical Biosensors for Nitrogen Monoxide and Carbon Monoxide," *Analyst* 120:2725–2730 (1995).
Dave et al., "Sol–Gel Encapsulation Methods for Biosensors," *Analytical Chemistry* 66(22):1120A–1127A (1994).

*Primary Examiner*—Leon B. Lankford, Jr.
*Attorney, Agent, or Firm*—Medlen & Carroll

[57] ABSTRACT

Fiberless optical sensors (plasticized PVC, acrylamide or gold particles) are described having a size ranging from between approximately 1 micrometer and 1 nanometer in diameter. The sensors comprise ionophores useful for the detection of intracellular analytes.

29 Claims, 4 Drawing Sheets

OPTICAL FIBERLESS SENSORS FOR ANALYZING CELLULAR ANALYTES

This invention was made with government support under MDA972-97-1-006 awarded by DARPA. The government has certain rights in the invention.

FIELD OF THE INVENTION

The invention relates generally to optical fiberless sensors, method of fiberless sensor fabrication and uses of such sensors in cells.

BACKGROUND

The ability of cells, tissues, an organ system and an entire organism to rapidly respond and adapt to exogenous stimuli is a requirement for the maintenance of life. Exposure of a single cell to such stimuli can manifest itself in a variety of ways, including a flux of essential intracellular ions (i.e. Na+, K+, Ca++, Cl−, H+), as well as changing oxygen and glucose levels. These changes can trigger additional signaling cascades, ultimately resulting in the recruitment of the appropriate cellular machinery for a response to the stimuli.

Of course, some stimuli are pathogenic to cells. Such stimuli cause a combination of linked and cascading biochemical events leading up to disease and/or cell death. For example, exposure to bacteria, viruses, toxins and toxicants may result in a myriad of intra/extracellular responses, depending on the pathogen or pathogenic agent in question and the route of exposure. The determination and understanding of which of the "downstream" biochemical signals elicited are indicators of physical, chemical or mechanical injury are fundamental to the development of countermeasures and therapy.

Classical biochemical investigations of the toxicologic effects of chemicals on organs and tissues were typically performed on homogenates. This approach reduced complex arrays of cells to a uniform blend. While providing important new information on fundamental mechanisms of toxicology/pharmacology, these studies are limited in their ability to discriminate between cells which are passively or actively involved.

More recent molecular and imaging techniques have improved cellular resolution. However, these newer imaging techniques frequently provide only static "snapshots" of dynamic cellular processes. Other approaches, while more dynamic, suffer from the fact that the approach alters the cells under study. For example, commercially available fluorescent probes used in the detection of calcium fluxes, chemically bind the moiety in question and potentially alter its homeostasis in situ.

Clearly, the most extensive work done intracellularly focused on the direct injection of dyes into the cell. While this method has provided researchers with a simple technique to study cellular processes, it has also proven problematic. For instance, the dye may itself be toxic, or otherwise interfere with the cell chemistry. Another problem is that there is no way to position the dye once it is introduced into the cell. Often, the dye is selectively trapped in some organelles, rather than dispersed evenly throughout the cell.

An additional, critical limitation with the dye injection approach is that the technology is currently limited in selectivity to a small number of analytes. For instance, while there are good dyes for calcium ion detection, there are none for potassium, sodium or chloride.

Fiber optic probes, or optodes, with a polymer sensing element, solve the above problems of dye injection. See W. Tan et al., "Submicrometer Intracellular Chemical Optical Fiber Sensors," *Science* 258:778 (1992). These microfiberoptic sensors (100–1000 nm) are based on optical grade silica fibers pulled to submicron size. The pulled fiber tips are much less fragile than those of the electrochemical microsensors, which are made from pulled micropipettes. Attached to the tip is a dye-polymer matrix, which is very durable and smooth and runs tightly bound to the tip, even during penetration of biological tissues. The matrix on the end of the fiber often includes several components, such as a chromoionophore, an ionophore, and appropriate ionic additives, all trapped inside a polymer layer, so that no chemicals are free to diffuse throughout the cell. The effects of toxicity of the dyes are thus minimized. Also, the probe can be carefully positioned in the cell, allowing any specific area to be imaged or monitored.

Nonetheless, the fiber optic probes have the significant drawback of being unable to easily monitor more than one location in the cell. For monitoring more than one location, multiple probes are needed. Due to size constraints, it can prove difficult to position several fibers inside a single cell. Moreover, even the insertion of single fiber sensor can easily damage a cell or short out the cross membrane electrical potential and having several fibers compounds this problem.

Thus, improved methods for studying cells and intracellular analytes are needed. Such improved methods should be amenable to monitoring the cell at more than one location and should have minimal toxicity.

SUMMARY OF THE INVENTION

The invention relates generally to optical fiberless sensors, method of fiberless sensor fabrication and uses of such sensors in cells. The sensors of the present invention are: (1) small enough to enter a single mammalian cell relatively non-invasively, (2) fast and sensitive enough to catch even minor alterations in the movement of essential ions and (3) mechanically stable enough to withstand the manipulation of the sensor to specific locations within the cell.

Importantly, the fiberless sensors of the present invention are non-toxic and permit the simultaneous monitoring of several cellular processes. In one embodiment, the present invention contemplates the use of such fiberless sensors to monitor a single cell exposed to a variety of noxious or trophic stimuli.

The fiberless sensors of the present invention are particularly useful for the direct, real-time, non-invasive, intracellular studies of chemical insults and in elucidation of subcellular mechanisms of action induced by pathogens and related toxins. These sensors are immensely smaller, faster and more sensitive than fiber-optic sensors currently used. The spatially and temporarily highly resolved and highly detailed chemical information gained from using these sensors, greatly speeds up current protocols of research and also leads to new and improved methodologies.

In one embodiment, the present invention contemplates a method comprising: a) providing i) one or more cells, ii) a plurality of fiberless optical sensors, and iii) a means for detecting said sensors; b) introducing said plurality of sensors into said one or more cells; and c) detecting said sensors in said cells with said detecting means.

In another embodiment, the present invention contemplates a method comprising: a) providing i) one or more cells, ii) a plurality of fiberless optical sensors, iii) an exogenous cellular stimulus, and iv) a means for detecting said sensors; b) introducing said plurality of sensors into said one or more cells; c) stimulating said one or more cells with said exogenous cellular stimulus, and d) detecting said sensors in said cells with said detecting means.

In one embodiment, the present invention contemplates a method comprising: a) providing i) first and second preparations of cells, ii) a plurality of fiberless optical sensors, iii) an exogenous cellular stimulus, and iv) a means for detecting said sensors; b) introducing said plurality of sensors into said first and second preparations of cells; c) stimulating said first preparation of cells with said exogenous stimulus, d) detecting said sensors in said cells with said detecting means, and e) comparing the sensors in said first preparation of cells with the sensors in said second preparation of cells.

It is not intended that the present invention be limited by the nature of the cells. Both prokaryotic and eukaryotic cells can be monitored using the sensors of the present invention. Among eukaryotic cells, it is specifically contemplated that the sensors of the present invention are introduced into mammalian cells. All types of mammalian cells are contemplated (e.g. oocytes, epithelial cells, etc.). In some embodiments, cells such as neurons and astrocytes in primary culture are contemplated. Thus, the present invention contemplates generally compositions comprising mammalian cells containing fiberless optical sensors.

In one embodiment, the fiberless sensors are used in the eye. This readily permits monitoring of responses to agents coming in contact with the eye (e.g. gases, aerosols, etc.). In another embodiment, the fiberless sensors are used in the cardiovasculature. This readily permits cardiac monitoring.

It is also not intended that the present invention be limited by the precise composition of the fiberless sensors. The fiberless sensors of the present invention are either solid or semisolid particles ranging in size between approximately 5 micrometer and 1 nanometer in diameter. The ultimate small size is attained by fine grinding and filtering or by microemulsion techniques used to form mono-disperse colloidal particles (rather than nano-fabrication). In one embodiment, the sensor is selected from the group consisting of polymer fiberless sensors, acrylamide fiberless sensors, and metal fiberless sensors.

In one embodiment, the polymer fiberless sensors of the present invention comprise an ionophore, a chromoionophore and a polymer. It is not intended that the present invention be limited to a particular polymer. In one embodiment, the polymer is selected from the group consisting of poly(vinyl chloride), poly(vinyl chloride) carboxylated and poly(vinyl chloride-co-vinyl acetate-co-vinyl alcohol). In a preferred embodiment, the polymer fiberless sensors further comprise an additive and a plasticizer.

In one embodiment, the acrylamide fiberless sensors of the present invention comprise polyacrylamide and a reactive dye. In a preferred embodiment, the acrylamide fiberless sensors further comprise N,N-methylenebi-(acrylamide) and the mixture is polymerized to a gel.

In one embodiment, the metal fiberless sensors of the present invention comprise protein (or peptide) in combination with a metal selected from the group consisting of gold, silver, platinum and alloys thereof. In one embodiment, the protein (or peptide) is dye-labeled (e.g. with FITC).

Regardless of the sensor type (e.g. metal or polymer), the fiberless sensor of the present invention is contemplated to be capable of measuring intracellular analytes, and more particularly, capable of detecting a change in the concentration of intracellular analytes. It is not intended that the present invention be limited to specific analytes.

Nonetheless, preferred analytes measured by the sensors of the present invention include, but are not limited to, intracellular ions (i.e. Na+, K+, Ca++, Cl−, H+), as well as oxygen and glucose.

It is not intended that the present invention be limited by the manner in which the sensors of the present invention are introduced into cells. In one embodiment, a buffered suspension of fiberless sensors is injected into the sample cell with a commercially-available pico-injector. In another embodiment, the fiberless sensors of the present invention are shot into a cell with a commercially-available particle delivery system or "gene gun" (such gene guns were developed and are now routinely used for inserting DNA into cells).

In some embodiments, the fiberless sensors of the present invention are positioned with in a cell or remotely steered into a cell, by photon pressure or "laser tweezers". This technique uses an infra-red laser beam which traps the particles. Alternatively, the particles can be moved magnetically, by remotely steering magnetic nanoparticle pebbles (commercially available) into a cell.

It is also not intended that the present invention be limited by the detecting means. In one embodiment, the fiberless sensors of the present invention are addressed by laser beams (rather than fibers), and their fluorescent signals are collected and analyzed by procedures identical to those used for the fiber-tip nanosensors. See U.S. Pat. Nos. 5,361,314 and 5,627,922 to Kopelman et al., hereby incorporated by reference.

DEFINITIONS

To facilitate understanding of the invention, a number of terms are defined below.

An "allergic reaction" is any abnormal or altered reaction to an antigen (or "allergen"). Typically this reaction is characterized by hypersensitivity of the body to specific substances, whether protein, lipid or carbohydrate in nature. Allergic reactions may be local, such as contact dermatitis, or may be systemic, such as anaphylaxis. Among allergic diseases, bronchial asthma is one of the most significant. In most urban hospitals, it is the leading cause of admission of children. Current medical practice accepts asthma in afflicted individual to be an unavoidable, incurable illness.

The term "analyte" is intended to comprise any substance within a cell. Analytes of particular interest include (but are not limited to) intracellular ions (i.e. Na+, K+, Ca++, Cl−, H+), as well as oxygen and glucose.

The term "chemical reaction" means reactions involving chemical reactants, such as inorganic compounds.

The phrase "exogenous cellular stimulus" means a stimulus exogenous to a cell that is capable of stimulating the cell.

By "stimulating the cell" is meant that the status of the intracellular analytes of the cell is changed (e.g. the concentration is changed).

Such stimuli include, but are not limited to a variety of noxious, pathogenic and trophic stimuli. In one embodiment, the stimulus is a toxic agent (or "toxicant"). In another embodiment, the toxic agent is a biological toxin.

It is not intended that the present invention be limited to particular toxins. For example, prokaryotes are a known source of a variety of toxins. Among species of bacteria, the most notorious toxin sources are certainly *Clostridum botulinum* and *Clostridium parabotulinum*. The species produce the neurogenic toxin known as botulinus toxin. While a relatively rare occurrence in the United States, involving only 355 cases between 1976 and 1984 (K. L. MacDonald et al., *Am. J. Epidemiology* 124, 794 (1986)), the death rate due to the botulism toxin is 12% and can be higher in particular risk groups. C. O. Tacket et al., *Am. J. Med.* 76, 794 (1984).

Many other bacteria produce protein toxins of significance to humans, including *Bacillus anthracis, Bordetella pertussis* (diptheria), *Pasteurella pestis, Pseudomonas aeruginosa, Streptococcos pyrogenes, Bacillus cereus, E. coli,* Shigella, *Staphylococcus aureus, Vibrio cholerae,* and *Clostridium tetani.* Thorne and Gorbach, Pharmacology of Bacterial Toxins, In: International Encyclopedia of Pharmacology and Therapeutics, F. Dorner and J. Drews (eds.), Pergamon Press, Oxford (1986), pp. 5–16.

"Initiating a reaction" means causing a reaction to take place. Reactions can be initiated by any means (e.g. heat, wavelengths of light, addition of a catalyst, etc.)

The term "microorganism" as used herein means an organism too small to be observed with the unaided eye and includes, but is not limited to bacteria, viruses, protozoans, fungi, and ciliates.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

A "solvent" is a liquid substance capable of dissolving or dispersing one or more other substances. It is not intended that the present invention be limited by the nature of the solvent used.

DESCRIPTION OF THE INVENTION

The invention relates generally to optical fiberless sensors, method of fiberless sensor fabrication and uses of such sensors in cells. The fiberless sensors allows for direct insertion, without the need for buffering solutions, which could change the analyte contents inside a cell. The fiberless sensors have the advantages of fiber micro-optodes, but are much smaller, less invasive and totally encapsulated by the cell or even by one of its organelles. They also have the potential for multiple analyte measurements and multiple positioning inside a single cell.

The fiberless sensors of the present invention comprise one ore more active sensor molecule (e.g. calcium green) that is embedded in an inert host (e.g., acrylic polymer). These sensors have numerous advantages compared with individual molecular tags (e.g., calcium green), including but not limited to: (1) No toxicity or interference with cell chemistry; (2) No selective sequestration in subcellular organelles; (3) No lipophilicity requirement for "smuggling" the molecule across the membrane; (4) No ion buffering; (5) No quenching of fluorescence by heavy metals; (6) No dye loss through leakage; (7) No alteration of fluorescence by sample viscosity; (8) No poor resolution at cell edges. Most importantly, (9) the fiberless sensors allow parallel processing of multiple chemical analytes (most fluorescent tags do not allow this due to mutual interference by spectral overlap, fluorescence quenching and chemical interactions).

A. Optical Fiberless Sensors

The present invention contemplates fiberless sensors or Probes Encapsulated By BioListic Embedding (PEBBLEs). While a variety of such fiberless sensors are contemplated (including but not limited to metal particles), the preferred fiberless sensors of the present invention are finely ground or formed particles comprising polymer matrices that are incorporated with fluorescent dyes, ionophores, and/or other components. These sensors, with sizes ranging from the submicrometer to micrometer, can be made from any polymer matrix. A preferred polymer matrix comprises plasticized poly(vinyl chloride).

The fiberless sensors are particularly suitable for chemical analysis in mammalian cells, by inserting the sensors into the cell, and monitoring remotely. The sensor particles or beads can be dispersed in buffer solution and pico-injected into a cell. The particles can be monitored singly, in groups located at different positions, or several different kinds can be injected for simultaneous measurements of several distinct intracellular ion or small molecule concentrations.

The fiberless sensors circumvent many of the problems associated with optical fiber sensors. While the fiberless sensors of the present invention can be made of the same polymer matrix as that used on the end of an optode, they do not have the fiber size constraints and the associated consequences for the cell. A plurality of fiberless sensors of the present invention can be injected at one time, giving a means for simultaneous measurements. This can even be done with a single penetration, and the cell wall can be allowed to recover. The polymer matrices have been shown to have very little effect on the cell itself (such as toxicity), and can be left inside for the lifetime of the cell.

B. Sensor Fabrication

In one embodiment, the fiberless sensor of the present invention comprises several components, such as a chromoionophore, an ionophore, and appropriate ionic additives, all trapped inside a polymer layer, so that no chemicals are totally free to diffuse throughout the cell. The precise composition depends on which analyte (or analyte ion) is sought to be measured.

In one embodiment, the particle is prepared for each analyte by selecting one ionophore (30 mmol/kg), one chromoionophore (15 mmol/kg), one additive (15 mmol/kg), one polymer (33 wt %) and one plasticizer (66 wt %). This mixture should then be dissolved in solvent. The preferred solvent is freshly distilled THF (200 mg mixture in 5 mL THF). The solution can then be coated onto polystyrene spheres, and ground in liquid nitrogen.

It is not intended that the present invention be limited by the nature of the ionophore and/or chromoionophore. For e.g., Porphyrins (from Aldrich chemical), are dyes that can be used for oxygen sensors; Calixarenes and Cobyrinates are examples of ionophores that can be used for sodium and nitrite ions respectively. Other illustrative examples (allowing for mixing and matching) are provided in the tables below (all of the chemicals are commercially available; most are available from Fluka Chemical Corp, Ronkonkoma, N.Y.).

C. Uses Of The Present Invention

The invention will be useful for, among other things, in the identification of cellular and subcellular responses which lead to disease. The fields in which the fiberless optical sensors of the present invention will find application are vast, and include basic research, diagnosis, and treatment of disease. Direct benefits to humans and the environment include the development of new drugs, understanding the synergistic response to complex mixtures of pollutants, and prevention of

TABLE 1

ILLUSTRATIVE IONOPHORES

| Analyte Ion | Ionophore | Alternate Name |
|---|---|---|
| Primary amines | Amine Ionophore I | |
| Ammonium | Ammonium Ionophore I | |
| Barium | Barium Ionophore I | |
| Cadmium | Cadmium Ionophore I | ETH 1062 |
| Calcium | Calcium Ionophore I | ETH 1001 |
| | Calcium Ionophore II | ETH 129 |
| | Calcium Ionophore III | Calcimycin |
| | Calcium Ionophore IV | ETH 5234 |
| Carbonate | Carbonate Ionophore I | ETH 6010 |
| | Carbonate Ionophore II | ETH 6019 |
| | Carbonate Ionophore III | ETH 6022 |
| | Carbonate Ionophore IV | |
| Cesium | Cesium Ionophore I | |
| Chloride | Chloride Ionophore I | |
| | Chloride Ionophore II | ETH 9009 |
| Copper (II) | Copper (II) Ionophore I | o-XBDiBDTC |
| Hydrogen | Hydrogen Ionophore I | |
| | Hydrogen Ionophore II | ETH 1907 |
| | Hydrogen Ionophore III | |
| | Hydrogen Ionophore IV | ETH 1778 |
| Hydrogen Sulfite | Hydrogen sulfite Ionophore I | ETH 5444 |
| Lead | Lead Ionophore I | ETH 322 |
| | Lead Ionophore II | MBDiBDTC |
| | Lead Ionophore III | ETH 5435 |
| | Lead Ionophore IV | |
| | Lead Ionophore V | 15-Crown-5 |
| Lithium | Lithium Ionophore I | ETH 149 |
| | Lithium Ionophore II | ETH 1644 |
| | Lithium Ionophore III | ETH 1810 |
| | Lithium Ionophore IV | ETH 2137 |
| | Lithium Ionophore V | 12-Crown-4 |
| | Lithium Ionophore VI | 6,6-Dibenzyl-14-crown-4 |
| | Lithium Ionophore VII | |
| | Lithium Ionophore VIII | |
| Magnesium | Magnesium Ionophore I | ETH 1117 |
| | Magnesium Ionophore II | ETH 5214 |
| | Magnesium Ionophore III | ETH 4030 |
| | Magnesium Ionophore IV | ETH 7025 |
| Nitrite | Nitrite Ionophore I | * |
| | Nitrite Ionophore II | |
| | Nitrite Ionophore III | |
| Potassium | Potassium Ionophore I | Valinomycin |
| | Potassium Ionophore II | |
| | Potassium Ionophore III | BME-44 |
| Silver | Silver Ionophore I | |
| | Silver Ionophore II | MAO |
| | Silver Ionophore III | |
| | Silver Ionophore IV | |
| Sodium | Sodium Ionophore I | ETH 227 |
| | Sodium Ionophore II | ETH 157 |
| | Sodium Ionophore III | ETH 2120 |
| | Sodium Ionophore V | ETH 4120 |
| | Sodium Ionophore VI | |
| | Sodium Ionophore X | |

TABLE 1-continued

ILLUSTRATIVE IONOPHORES

| Analyte Ion | Ionophore | Alternate Name |
|---|---|---|
| Uranyl | Uranyl Ionophore I | ETH 295 |
| Zinc | Zinc Ionophore I | |

*(Cyanouqua-cobyrinic acid hepatokis 2 - phenylethyl ester)

TABLE 2

ILLUSTRATIVE CHROMOIONOPHORES

| Chromoionophores | Alternate Name |
|---|---|
| Chromoionophore I | ETH 5294 |
| Chromoionophore II | ETH 2439 |
| Chromoionophore III | ETH 5350 |
| Chromoionophore IV | ETH 2412 |
| Chromoionophore V | |
| Chromoionophore VI | ETH 7075 |
| Chromoionophore XI | ETH 7061 |

TABLE 3

ILLUSTRATIVE ADDITIVES

Cesium tetrakis(3-methylphenyl)borate
Potassium tetrakis[3,5-bis(trfluoromethyl)phenyl]borate
Potassium tetrakis(4-chlorophenyl)borate
Sodium tetrakis[3,5-bis(trfluoromethyl)phenyl]borate
Sodium tetrakis(4-fluorophenyl)borate Dihydrate
Sodium tetraphenylborate
Tetrabutylammonium tetraphenylborate
Tetradodecylammonium tetrakis(4-chlorophenyl)borate
Tetraheptylammonium tetraphenylborate
Tetraphenylphosphonium tetraphenylborate

TABLE 4

ILLUSTRATIVE PLASTICIZERS

| Plasticizors | Alternate Name |
|---|---|
| Benzyl ether | |
| Benzyl 2-nitrophenyl ether | |
| Bis(1-butylpentyl) adipate | |
| Bis(1-butylpentyl) decane-1, 10-diyl diglutarate | |
| Bis(2-ethylhexyl) adipate | |
| Bis(2-ethylhexyl) sebacate | DOS |
| 1-Chloronaphthalene | |
| Chloroparaffin | |
| 1-Decanol | |
| Dibutyl phthlate | |
| Dibutyl sebacate | |
| Dibutyltin dilaurate | |
| 1,2-Dimethyl-3-nitrobenzene | |
| Dioctyl phenylphosphate | |
| Dipentyl phthalate | |
| 1-Dodecanol | |
| Dodecyl 2-nitrophenyl ether | ETH 217 |
| [12(4-Ethylphenyl)dodecyl] 2-nitrophenyl ether | ETH 8045 |
| 2-Fluorophenyl 2-nitrophenyl ether | |
| 1-Hexadecanol | |
| 10-Hydroxydecyl butyrate | ETH 264 |
| 2-Nitrodiphenyl ether | |
| 2-Nitrophenyl octyl ether | o-NPOE |
| 2-Nitrophenyl pentyl ether | |
| 1-Octadecanol | |
| Octyl [2-(trifluoromethyl)phenyl] ether | ETH 5406 |
| 5-Phenyl-1-pentanol | |
| 1-Tetradecanol | |
| Tetraundecyl benzhydrol-3,3',4,4'-tetracarboxylate | ETH 2112 |

TABLE 4-continued

ILLUSTRATIVE PLASTICIZERS

| Plasticizors | Alternate Name |
| --- | --- |
| Tetraundecyl benzophenone-3,3',4,4'-tetracarboxylate | ETH 2041 |
| Tributyl phophate | |
| Trioctylphosphine oxide | |
| Tris(2-ethylhexyl) phosphate | |
| Tris(2-ethylhexyl) trimellitate | | developmental and degenerative disorders. Fiberless optical sensors will find application in any setting where current techniques assess whole organism (including but not limited to intraembryonic applications) or whole cell chemistry in an attempt to elucidate specific mechanisms of toxicity. The fiberless optical sensors will bring to light an entirely new level of detail not previously available.

1. Elucidate Responses to Toxicants

The responses to toxicants can be elucidated in developmental and adult models of toxicity in vitro, in utero, in vivo, or in slice single cell suspensions, mono or bi-layers, colonies. The types of toxicants that can be evaluated include bacterial, viral, prion, fungal, protozoan, plant, anthropogenic (pesticides, complex organic compounds used in manufacturing and their emissions and discharges, oxidants, environmental degradation products of natural and anthropogenic chemicals), synthetic and natural nutritional supplements, electromagnetic radiation, contact media (ingestion, inhalation, dermal, mucosal).

The fiberless sensors of the present invention can be used with success to assist in the identification of structure-activity relationships and chemical nature of toxicants inside and outside the cell. This information will provide predictive abilities for a myriad of applications including pesticide design, understanding the biochemical role of CFC substitutes on plants and animals prior to their mass production and release, and ultimately even setting regulations for toxicologically-significant levels of pollutants in air, water, and food.

In one embodiment, the present invention contemplates utilizing the intracellular analyte response pattern to identify identify the pathogenic/toxic agent. That is to say, the response to one type of toxic agent (or even a particular agent within a class of toxic agents) can be monitored for the pattern of intracellular analyte changes. Such a pattern becomes a "fingerprint" for exposure to that particular agent, allowing for more rapid treatment of the individual and/or prompt removal of the individual from the source or "zone" of exposure.

2. Development of Diagnostic Tools and Treatment of Disease

As noted above, the fiberless sensors of the present invention can be used to measure any alteration in endogenous analytes of any cell. The present invention specifically contemplates transcutaneous monitoring (e.g. ear, skin) as well as continuous flow monitoring of cells in culture, organotypic culture, organ slices, isolated perfused organs, organs in situ, and whole animal monitoring.

The present invention contemplates that the fiberless sensors of the present invention can be used as diagnostic tools for earlier intervention (i.e. earlier than currently available) and treatment of disease. Examples of where early intervention is important include, but are not limited to, allergic responses and septic shock.

Allergic Reponses

In one embodiment, the fiberless sensors are used to detect allergic responses. In this regard, inhalation of allergens by sensitized subjects typically results in an early phase response characterized by bronchoconstriction within 10 minutes of inhalation, reaching a maximum within 1 to 2 hours. In some subjects, the airway narrowing recurs after 3 to 4 hours (i.e., late phase), reaching a maximum during the next few hours. P. M. O'Byrne et al., *Am. Rev. Respir. Dis.* 136:740 (1987). This late phase is thought to be due to the cellular phase of inflammation. F. E. Hargreave et al., *Eur. J. Respir. Dis.* 69 (Suppl 147): 16 (1986). P. M. O'Byrne, *Chest* 90:575 (1986). J. Dolovich et al., *J. Allergy Clin. Immunol.* 83 (Suppl):521 (1987).

The present invention contemplates the use of fiberless optical sensors in the relevant cells of the allergic individual to allow for detection of an allergic response within seconds or (at most) minutes after exposure to an allergen. This allows for earlier intervention and treatment.

Sepsis and Septic Shock

Sepsis is a major cause of morbidity and mortality in humans and other animals. It is estimated that 400,000–500,000 episodes of sepsis resulted in 100,000–175,000 human deaths in the U.S. alone in 1991. Sepsis has become the leading cause of death in intensive care units among patients with non-traumatic illnesses. [G. W. Machiedo et al., *Surg. Gyn. & Obstet.* 152:757–759 (1981).] It is also the leading cause of death in young livestock, affecting 7.5–29% of neonatal calves [D. D. Morris et al., *Am. J. Vet. Res.* 47:2554–2565 (1986)], and is a common medical problem in neonatal foals. [A. M. Hoffman et al., *J. Vet. Int. Med.* 6:89–95 (1992).] Despite the major advances of the past several decades in the treatment of serious infections, the incidence and mortality due to sepsis continues to rise. [S. M. Wolff, *New Eng. J. Med.* 324:486–488 (1991).]

Sepsis is a systemic reaction characterized by arterial hypotension, metabolic acidosis, decreased systemic vascular resistance, tachypnea and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). Septicemia and septic shock (acute circulatory failure resulting from septicemia often associated with multiple organ failure and a high mortality rate) may be caused by a number of organisms.

The systemic invasion of microorganisms presents two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and oftentimes, death.

The present invention contemplates the use of fiberless sensors in patients at risk for septic shock. Introduction of the sensors in the patient's cells (e.g., lymphocytes) allows for earlier detection of toxin exposure and thus, prompt intervention.

3. Imaging

The fiberless sensors of the present invention are ideal for simultaneous realtime monitoring of many (e.g. six) chemical analytes as well as acting as parallel processors. They may also be used for spatially resolved information. The spatial distribution of the fiberless sensors in a cell can be observed with Laser Scanning Confocal Microscopy (LSCM). Of interest is whether any segregation occurs in one location of the cell preferentially over others. Cellular component labeling, 3-D imaging and visualization, can be done at an Imaging laboratory. Rearrangement of fiberless sensors following injection can be monitored by periodically acquiring a series of 3-D LSCM images. High resolution (100×NA 1.4) images can be obtained to determine analyte concentration and changes can be determined with subsection imaging of sensor locations. Several (2,3, or more) individual sensor locations can be identified within the small localized area of the cell where the pebbles are injected. Only those locations are then imaged confocally in order to follow in time (scale of hours) analyte changes after a biochemical perturbation. Significant photobleaching from such occasional scans, are not anticipated [i.e. the extremely small (micron or submicron) photoexcited region limits photo-damage to that region and enables fast diffusive replenishment from the dark environment]. Also, images can be obtained simultaneously at two or more wavelengths using an electronically tunable filter on a time scale of hours.

Utilizing the fiberless optical nanosensors of the present invention, one can get a chemical video for a single analyte (e.g. calcium), analogous to a black and white movie, or a chemical video of a list of chemical analyte (e.g., calcium, sodium, potassium, chloride, oxygen and pH), analogous to a color video or, alternatively, to six single color videos, each taken with a different narrow-band optical filter.

Figure 1:
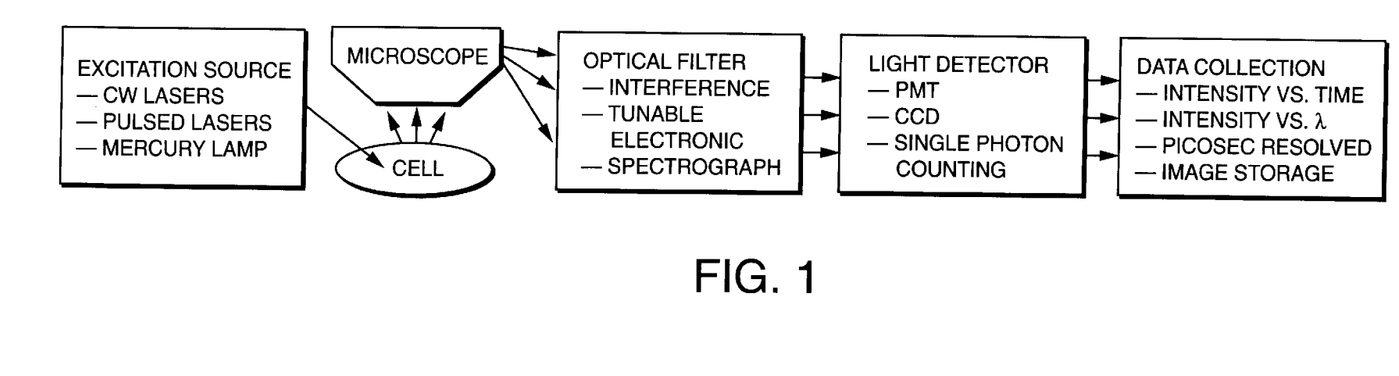
FIG. 1 schematically shows several embodiments of a detection system for detecting the fiberless optical sensors of the present invention.

For such monitoring, the cell is placed under a microscope objective lens (see FIG. 1), and may be immobilized by a micropipette (standard technique). One or several fiberless sensors are introduced into the cell(s) and are addressed optically by laser beams.

Generally, each fiberless sensor is uni-functional, but six or more kinds ("colors") of sensors can be introduced simultaneously. The time-resolved color images are collected on a CCD (charged coupled device) or equivalent optical detectors (see FIG. 1) and the digital information is deposited in an optical disk. Eventually the disk is processed and enhanced for optimal imaging and evaluation. Data can be processed in a variety of ways (intensity versus time, etc.).

DESCRIPTION OF PREFERRED EMBODIMENTS

One of the preferred embodiments of this invention is to use the fiberless optical sensors of the present invention for the measurement of solute fluxes in mammalian cell systems following exposure to external noxious stimuli. The sensors permits simultaneous measurement of multiple chemical species, effectively producing a "physiogram" of chemical alterations in a single cell. Several different approaches are contemplated to measure the solute fluxes in mammalian cell systems following exposure to external noxious stimuli, including but not limited to 1) the measurement of ionic/solute concentrations in normal respiring cells in suspension culture, 2) the measurement of ionic/solute fluxes in normal respiring cells in suspension culture, cells on substrates and tissue slices, and 3) the detection of specific alterations in intracellular ionic/solute concentrations and fluxes following exposure to pathogenic stimulus and modulation with pharmacologic agents.

In Vivo and Ex Vivo Applications

The present invention also contemplates application of fiberless sensors to in vivo measurements for time-resolved monitoring of specific anatomically distinct regions of the cell under both natural and toxic conditions. The present invention also contemplates ex vivo measurements (e.g. using cells outside the body on a patch) for detecting exposure to toxic conditions.

Pharmacological Agents

In some of the embodiments of this invention, pharmacologic agents can be used for the manipulation of ionic fluxes. The glucose kinase inhibitors, 2-dioxy-D-glucose or 2-cyclohexen-1-one can be used to inhibit glucose utilization in tissue slices and cells in culture (Parry and Walker, 1966; Miwa et al., 1990). Levels of nitric oxide in solution can be manipulated by incubation of biological specimens with the nitric oxide synthase inhibitor NG-monomethyl-L-arginine (Mulligan et al., 1991).

Manipulating And Positioning The Sensors

In one embodiment, the present invention contemplates moving the fiberless sensors within a cell. Movement can be achieved with magnets or with an optical force trap ("laser tweezers").

The laser optical force trap (laser tweezers) was originally developed to hold and manipulate small dielectric particles, and later, atoms and molecules. The optical force trap can immobilize and manipulate small particles, including the fiberless sensors of the present invention, in aqueous solutions.

The operation of laser tweezers depends upon gradient forces of radiation pressure generated in a convergent cone of laser light. A laser beam is directed into a light microscope objective of high numerical aperture and is focused into a diffraction-limited spot in the field of view of the objective. Small dielectric particles are attracted to the center of the spot and are held there by the scattering and gradient forces. The magnitude of the force holding the particles in the spot depends partially upon the difference between the refractive indexes of the particles and its surrounding environment; generally, the technique is capable of generating a few microdynes of force. Movement of the laser beam will tend to move any trapped particles with the light beam. The technique is non-ablative: the wavelength of laser light is selected for extremely low absorption by the material being manipulated, and the small amount of energy that is absorbed by the material is dissipated into the surrounding aqueous medium.

EXPERIMENTAL

The following examples serve to illustrate certain preferred embodiments and aspects of the present invention and are not to be construed as limiting the scope thereof. In the experimental disclosure which follows, the following methodology apply.

Reagents for the PVC PEBBLEs: Poly(vinyl chloride) (PVC), chromoionophore II (ETH 2439) and 2-nitrophenyl octyl ether (o-NPOE) were obtained from Fluka Chemical Corp (Ronkonkoma, N.Y.). The fluorescent label 1,1'-dioctadecyl-3,3,3',3'-tetramethylindocarbocyaine perchlorate (DiIC$_{18}$) was obtained from Molecular Probes, Inc. (Eugene, Oreg.). Sterile phosphate buffer (pH 7.4) was obtained from Fisher Chemicals (Pittsburgh, Pa.).

Preparation of the PVC PEBBLEs: Membranes contained 33% PVC and 66% o-NPOE by weight. All components were dissolved in freshly distilled tetrahydrofuran (THF). The fiberless sensors were prepared by drying and crushing small (50 nm) polystyrene nanospheres and coating with the PVC cocktail. When dry, the nanospheres were crushed again, to break up the membrane. Due to the nature of the PVC matrix, the membrane could not be crushed directly into small pieces without the introduction of the polystyrene beads. The particles were 1–5 μm in size.

Figure 2:
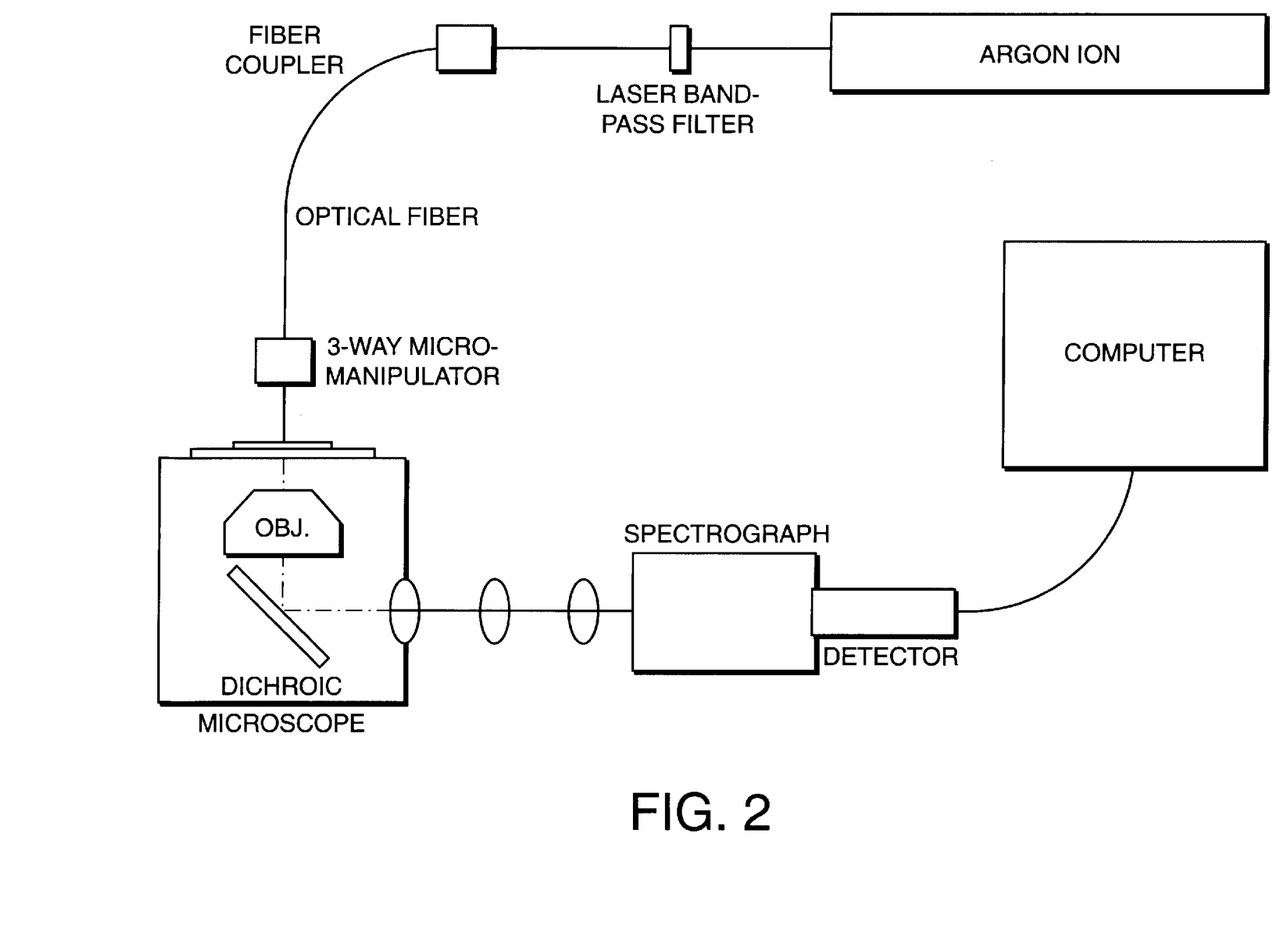
FIG. 2 schematically shows one given embodiment of a detection system for detecting the fiberless optical sensors of the present invention.

Optics: The complete optical path (see FIG. 2) included: Ion Laser Technology (Salt Lake City, Utah) argon ion laser; 514.5 nm laser band-pass filter (Newport Corp. Irvine, Calif.); Uniblitz shutter controller (Rochester, N.Y.); fiber coupler (Newport Corp. Irvine, Calif.); Olympus inverted fluorescence microscope, IMT-II (Lake Success, N.Y.); Nikon 50 nm f/1.8 camera lenses; Acton 150 mm spectrograph (Acton, Mass.); and, a Princeton Instruments 1024×256 LN2 cooled CCD array (Trenton, N.J.).

Figure 3:
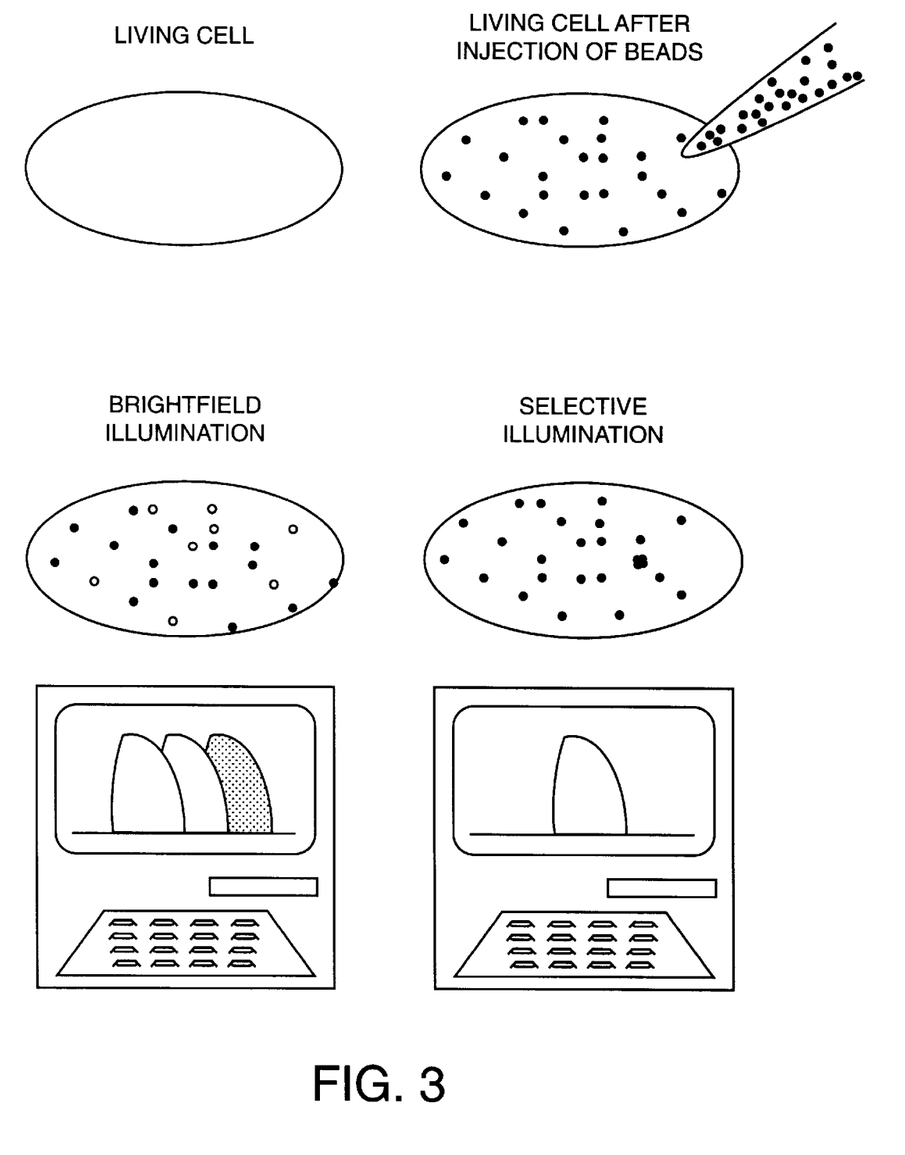
FIG. 3 schematically shows the introduction of the optical fiberless sensors of the present invention into cells.

Biolistics Particle Delivery System: A Biolistic PDS-1000/ He System (bench-top model) from Bio-Rad (Hercules, Calif.) with grade 5 helium was used to inject the cells with the fiberless sensors of the present invention (FIG. 3). Sample preparation for the particle delivery system required dispersion of the polymer beads in water, and the careful application of a thin film of beads onto the target membrane. Low firing pressures were used, with the best results being obtained at 1100 psi, with a vacuum of 15 torr on the system. Repeated rinsing was performed to ensure that sensors not in the cells were removed from the sample. The cells were analyzed within a few hours.

Cell Lines: Stocks of human SY5Y neuroblastoma and C6 glioma cells (American Type Cell Culture cell bank) are maintained in culture according to recommended protocols supplied by ATCC.

EXAMPLE 1

In this example, fiberless optical sensors have been prepared for the intracellular monitoring of ion or small molecule concentrations. As noted previously, the sensors are made from a pulverized matrix (plasticized PVC, acrylamide or gold), containing fluorescent dye molecules and non-fluorescent ionophores coated onto a polystyrene nanosphere. In this example, single sensors, on the order of 1–5 $\mu$m (see the fabrication methods described above), were inserted into human neuroblastoma cells with a particle delivery system.

Neuroblastoma cells (cell line SH-SY5Y) were plated into 60 mm petri dishes and incubated in a $CO_2$ environment. The cells were used when they reached a confluency of about 80%. Phosphate buffer was removed from the cells before sensor injection, then immediately replaced to prevent the cells from dying out.

Figure 4:
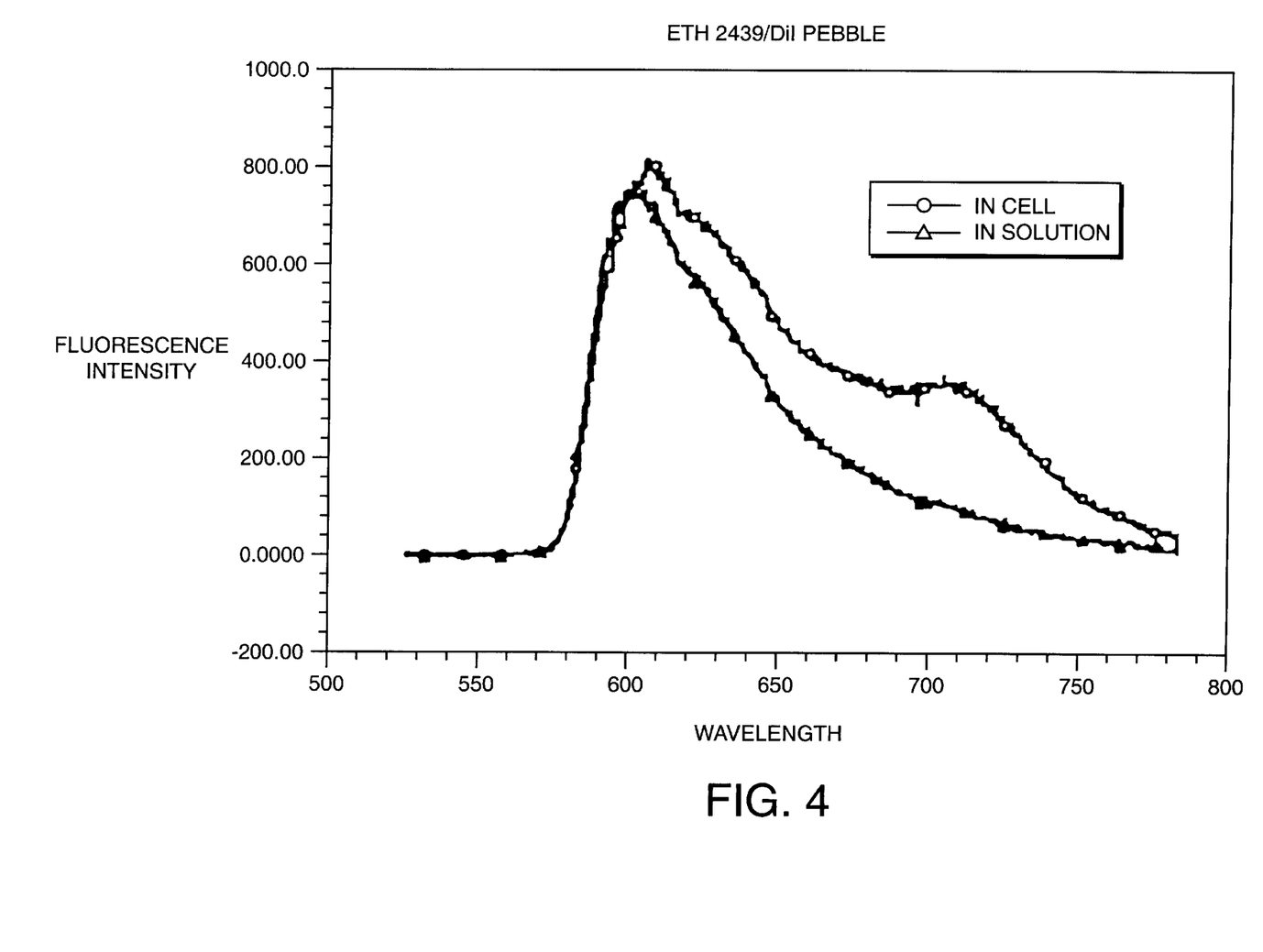
FIG. 4 shows the fluorescence spectrum of one embodiment of a fiberless sensor of the present invention when inside and outside a cell.

The pH sensitive dyes were found to be ideal indicators for the location of the sensor; they changed color, depending on whether the probe was inside or outside the cell. The system allowed for direct insertion, without the need for buffering solutions, which would have changed the analyte contents inside a cell. The fiberless sensors had the advantages of fiber micro-optodes, but were much smaller, less invasive and totally encapsulated by the cell or even by one of its organelles. They also had the potential for multiple analyte measurements and multiple positioning inside single cells. The composition (ETH 2439/DiI) used was a good indicator of the location of the sensor in the sample. Without an environmentally sensitive dye, it is difficult to differentiate a sensor that is encapsulated inside a cell from one that is embedded in a cell wall or even free in solution. As apparent from the spectra in FIG. 4, the sensor composition provided a method of determining the location of a sensor within the cell spectroscopically.

Sophisticated equipment (cooled CCD, spectrometer, etc.) was not necessary to obtain preliminary information from micron-sized sensors used in this example. Indeed, the sensors could also be illuminated with a mercury arc lamp, viewed with the aid of a microscope, and easily photographed with a standard camera. The red color of the sensors the cell was clearly visible inside the cell walls. Also, the green sensors that were floating free in solution, were easily seen. The ability to visually analyze the sensors provided a quick way to find sensors in regions of interest and also enabled the positioning of the sample for further spectral analysis.

The spectra (FIG. 4) clearly showed that there was a difference in pH between the intracellular environment and the surrounding buffer solution. The sensor inside the neuroblastoma cells produced a spectrum that was indicative of a relatively acidic environment compared to that of the buffer. The buffer solution, produced a spectrum indicating a relatively basic environment compared to that inside the cell. The spectra taken was that of a single sensor in a single cell, or a singe sensor floating in the solution. This example illustrates that fiberless optical sensors produced a fluorescence powerful enough even at a size (1–2 $\mu$m), and was small enough to fit inside a mammalian cell without any apparent perturbation.

EXAMPLE 2

In this example, involves stimulating cells containing fiberless sensors with an exogenous cellular stimulus and detecting the sensors in the stimulated cells. In this example, lipopolysaccharide (LAPS) is used as the exogenous stimulus. LAPS is produced by a variety of pathogenic microorganisms. LAPS has been shown to stimulate a variety of biochemical signaling pathways in the immune system, skin, lung, brain, neuroendocrine and neuro-immune axes, cardiac muscle and other mammalian systems. Among other effects, LAPS induces oxidative injury and increases cellular glutathione content. LAPS as the etiologic agent which initiates ionic/solute cascades can be used.

Using lymphocytes, the alterations in the regional cellular content of NO, Cl, Na+, H+ and glucose are monitored following exposure to LAPS. Independent confirmation of changes in the levels of ions/solute can be obtained by the use of pharmacologic agents which are known to interact with specific channels or receptors for the chemical species in question.

EXAMPLE 3

In this Example, fiberless sensors are introduced into oocytes. The mouse oocyte provides a large "target" (45–80 um in diameter) into which the fiberless optical sensors of the present invention can be injected. The use of oocytes permits the exploitation measurement of large ionic fluxes which may be toxicologically and pharmacologically induced in the cell. Oocytes possess several molecular mechanisms for the restoration of ionic equilibria such as pH. Three major transport systems exist to regulate the ionic strength and pH of the oocyte: (i) ATP-dependent pumps, (ii) channels and carriers which facilitate diffusion of ions across the plasmalemma, and (iii) exchanges which translocate two or more ions down a gradient. In addition to these ionic fluxes, the mouse oocyte has a number of second messenger systems which are directly linked to maturation processes. These include cAMP and inhibitors of cAMP signaling. The mammalian oocyte in situ exists within a dynamic follicular environment to which it responds with a myriad of intracellular ionic events.

Large numbers (20–30) of mouse oocytes can be obtained from 3–6 week-old mice. Briefly, 2–5 I.U. pregnant mares's serum gonadotropin (PMSG, "Gestyl"; Organanon) and human chorionic gonadotropin (hCG, Sigma) is administered i.p. hCG can be given 44–48 h after the priming dose of PMSG and the unfertilized ova collected by flushing the freshly excised oviducts 12–14 h after hCG. Oocytes collected can be used without further preparation in Hank's Balanced Salt Solution (HBSS).

The fiberless sensors can be introduced into the oocytes using the Biolistics Particle Delivery System (described above). The sensors can be detected visually or spectrophotometrically.

EXAMPLE 4

In this example, measurements are made in neural cells following an in vivo intravenous infusion of LAPS to mice. Briefly, a solution of LAPS (50–1,000 ng) in physiological saline can be injected into the femoral vein of the mouse. Physiological processes are halted by irradiating the head with 10 kW microwave for 0.5 sec (Cober Electronics Metabolic Vivostat, Conn.) and immediate immersion in liquid nitrogen. Cerebella and hippocampi are dissected and homogenized in deionized water for in vitro analysis of ions using the fiberless optical sensors of the present invention.

EXAMPLE 5

In this example, acrylamide fiberless sensors are fabricated. The polymerization solution consisted of 0.4 mM reactive dye, 27% acrylamide, 8% N,N-methylene-bis (acrylamide), and in 0.1 M phosphate buffer, pH 6.5. To 1 mL of solution was added 20 μL of N,N,N',N'-tetraethyldiethylenetriamine and heated at 60° C. for a few minutes. The resulting gel was allowed to cool, and the excess liquid evaporate. The polymer was crushed with the aid of liquid nitrogen.

A variety of reactive dyes (commercially available from Molecular Probes, Inc.) can be used with the acrylamide sensors, including but not limited to 5-(and 6-)-carboxynaphthofluorescein ("CNF"), 5-(and 6-)-carboxyfluorescein, SNAFL™-dextran, SNARF™-dextran, HPTS-dextran, BCECF-dextran, Fluorescein-dextran, Rhodal Green-dextran, DM-NERF-dextran, Oregon Green-dextran, and Cl-NERF-dextran.

EXAMPLE 6

In this example, metal fiberless sensors are fabricated. Such sensors are made by combining 0.1% protein or peptide (by weight) in colloid solution. Spontaneous adsorption of the protein to the metal surface takes place within minutes. A variety of colloids can be used, including but not limited to, colloids of gold, silver, platinum and gold/silver alloy. A variety of proteins and peptides can also be used, including but not limited to Cytochrome c' (isolated by Terry Meter and Michael Cusanovich, University of Arizona), Horseradish Peroxidase (Sigma), Cytochrome c (Sigma), Phycobiliproteins (Molecular Probes, Inc), Zinc fingers, Dye-labeled proteins (Dyes available from Molecular Probes). Among dye-labeled proteins, FITC, Fluorescein, Oregon Green,Tetramethylrhodamine, Rhodamine Red and Texas Red can be used.

From the above, it should be clear that the fiberless optical sensors of the present invention offer a number of advantages over existing technologies for the detection of intracellular analytes. Importantly, the sensors permit monitoring of the cell at more than one location with no (or minimal) toxicity.

We claim:

1. A composition, comprising cells containing at least one fiberless optical sensor, wherein said fiberless optical sensor comprises a solid particle ranging in size between approximately 1 micrometer and 1 nanometer in diameter wherein said particle comprises one or more active sensor molecules that are imbedded in an inert host.

2. The composition of claim 1, wherein said cells are eukaryotic cells.

3. The composition of claim 2, wherein said cells are mammalian cells.

4. The composition of claim 1, wherein said host is a polymer.

5. The composition of claim 4, wherein said polymer is selected from the group consisting of poly(vinyl chloride), poly(vinyl chloride) carboxylated and poly(vinyl chloride-co-vinyl acetate-co-vinyl alcohol).

6. The composition of claim 5, wherein said sensor molecule is an ionophore.

7. The composition of claim 6, wherein said sensor molecule is a chromoionophore.

8. The composition of claim 7, wherein said fiberless optical sensor further comprises an additive selected from the group consisting of cesium tetrakis(3-methylphenyl) borate, potassium tetrakis[3,5-bis(trifluoromethyl)phenyl] borate, potassium tetrakis(4-chlorophenyl)borate sodium tetrakis[3,5-bis(trifluoromethyl)phenyl]borate, sodium tetrakis(4-fluorophenyl)borate dihydrate, sodium tetraphenylborate, tetrabutylammonium tetraphenylborate, tetradodecylammonium tetrakis(4-chlorophenyl)borate, tetraheptylammonium tetraphenylborate, and tetraphenylphosphonium tetraphenylborate.

9. The composition of claim 8, wherein said fiberless optical sensor further comprises a plasticizer.

10. A method for detecting an analyte in a cell, comprising:
    a) providing i) one or more cells containing an analyte, ii) a plurality of synthetic fiberless optical sensors, wherein said fiberless optical sensors comprise solid particles ranging in size between approximately 1 micrometer and 1 nanometer in diameter wherein said particle comprises one or more active sensor molecules that are imbedded in an inert host, iii) an exogenous cellular stimulus, and iv) a means for detecting said sensors;
    b) introducing said plurality of sensors into said one or more cells;
    c) stimulating said one or more cells with said exogenous cellular stimulus; and
    d) detecting a response of said sensors in the presence of said analyte to said stimulating of said cells with said detecting means.

11. The method of claim 10, wherein said cells are eukaryotic cells.

12. The method of claim 11, wherein said cells are mammalian cells.

13. The method of claim 10, wherein said host is a polymer.

14. The method of claim 13, wherein said polymer is selected from the group consisting of poly(vinyl chloride), poly(vinyl chloride) carboxylated and poly(vinyl chloride-co-vinyl acetate-co-vinyl alcohol).

15. The method of claim 14, wherein said sensors molecule is an ionophore.

16. The method of claim 15, wherein said sensors molecule is a chromoionophore.

17. The method of claim 16, wherein said fiberless optical sensors further comprise an additive.

18. The method of claim 17, wherein said fiberless optical sensors further comprise a plasticizer.

19. A method for comparing analytes in cells, comprising:
    a) providing i) first and second preparations of cells containing an analyte, ii) a plurality of synthetic fiberless optical sensors, wherein said fiberless optical sensors comprise solid particles ranging in size between approximately 1 micrometer and 1 nanometer in diameter wherein said particle comprises one or more active sensor molecules that are imbedded in an inert host, iii) an exogenous cellular stimulus; and iv) a means for detecting said sensors;

b) introducing said plurality of sensors into said first and second preparations of cells;

c) stimulating said first preparation of cells with said exogenous stimulus;

d) detecting a response of said sensors in the presence of said analyte to said stimulating of said first preparation of cells with said detecting means; and e) comparing the sensors in said first preparation of cells with the sensors in said second preparation of cells.

20. The method of claim 19, wherein said cells are eukaryotic cells.

21. The method of claim 20, wherein said cells are mammalian cells.

22. The method of claim 19, wherein said host is a polymer.

23. The method of claim 22, wherein said polymer is selected from the group consisting of poly(vinyl chloride), poly(vinyl chloride) carboxylated and poly(vinyl chloride-co-vinyl acetate-co-vinyl alcohol).

24. The method of claim 23, wherein said sensors molecule is an ionophore.

25. The method of claim 24, wherein said sensors molecule is a chromoionophore.

26. The method of claim 25, wherein said fiberless optical sensors further comprise an additive.

27. The method of claim 26, wherein said fiberless optical sensors further comprise a plasticizer.

28. The method of claim 19, wherein said stimulus is a toxin.

29. The method of claim 28, wherein said toxin is a bacterial toxin.

* * * * *